(12) United States Patent
Hugg et al.

(10) Patent No.: US 10,598,801 B2
(45) Date of Patent: Mar. 24, 2020

(54) MODULAR GAMMA IMAGING DEVICE

(71) Applicant: KROMEK GROUP, PLC

(72) Inventors: James William Hugg, Mars, PA (US); Brian William Harris, Gibsonia, PA (US); Franklin Dean Walker, San Dimas, CA (US); Sarah Melissa Thomson, Pittsburgh, PA (US); Brian Patrick McVay, Waxhaw, NC (US); Rolf Martin Clajus, Los Angeles, CA (US)

(73) Assignee: KROMEK GROUP, PLC, Sedgefield (GB)

( * ) Notice: Subject to any disclaimer, the term of this patent is extended or adjusted under 35 U.S.C. 154(b) by 0 days.

(21) Appl. No.: 15/788,556

(22) Filed: Oct. 19, 2017

(65) Prior Publication Data

US 2019/0120978 A1    Apr. 25, 2019

(51) Int. Cl.
*G01T 1/36* (2006.01)
*G21F 1/08* (2006.01)
(Continued)

(52) U.S. Cl.
CPC .............. *G01T 1/243* (2013.01); *G01T 1/249* (2013.01); *H01L 27/14618* (2013.01);
(Continued)

(58) Field of Classification Search
CPC ....... A61B 6/037; A61B 6/0407; A61B 6/035; A61B 6/0457; G01T 1/243; H01L 31/115;
(Continued)

(56) References Cited

U.S. PATENT DOCUMENTS

| 4,272,680 A | 6/1981 | Cotic |
| 5,309,323 A * | 5/1994 | Gray .................... H05K 7/1411 |
| | | 312/332.1 |

(Continued)

FOREIGN PATENT DOCUMENTS

| WO | WO9620412 A1 | 7/1996 |
| WO | WO2015092630 A1 | 6/2015 |

OTHER PUBLICATIONS

European Patent Office, International Search Report, dated Mar. 28, 2019, 8 pages.

*Primary Examiner* — Taeho Jo
(74) *Attorney, Agent, or Firm* — Ference & Associates LLC

(57) ABSTRACT

One embodiment provides an imaging device, including: an enclosure comprising a casing and a radiation lining arranged within the casing to provide a radiation shield, wherein the enclosure comprises a removable portion; a plurality of modular components; each of the plurality of modular components comprising a plurality of gamma detectors including semiconductor crystals and being removable from the imaging device; the plurality of modular components being arranged such that the plurality of gamma detectors are configured in an array configuration with each of the plurality of gamma detectors having a predetermined spacing from each other gamma detector; a plurality of electronic communication components, wherein the plurality of electronic communication components facilitate communication from each of the gamma detectors to a processor using a hierarchical communication technique; and a cooling system. Other aspects are described and claimed.

21 Claims, 7 Drawing Sheets

(51) Int. Cl.
*G01T 1/24* (2006.01)
*H01L 27/146* (2006.01)
*H01L 31/024* (2014.01)
*H01L 31/0296* (2006.01)
*A61B 6/04* (2006.01)
*A61B 6/03* (2006.01)

(52) U.S. Cl.
CPC .. *H01L 27/14623* (2013.01); *H01L 27/14661* (2013.01); *H01L 31/024* (2013.01); *H01L 31/0296* (2013.01); *H01L 31/02966* (2013.01); *A61B 6/035* (2013.01); *A61B 6/037* (2013.01); *A61B 6/0407* (2013.01); *A61B 6/0457* (2013.01)

(58) Field of Classification Search
CPC ......... H01L 27/14663; H01L 27/14612; H01L 27/1443; H01L 27/14603; H01L 27/14609; H01L 27/14636; H01L 31/02164; H01L 31/035272; H01L 31/102; H01L 31/107; H01L 31/18; H01L 31/1804; H01L 27/14618; H01L 27/14623; H01L 27/14661; H01L 31/024; H01L 31/0296; H01L 31/02966
USPC .................................................... 250/370.09
See application file for complete search history.

(56) References Cited

U.S. PATENT DOCUMENTS

| | | | | |
|---|---|---|---|---|
| 5,668,851 A * | 9/1997 | Dobbs | ................... | G01T 1/1648 378/154 |
| 5,751,000 A * | 5/1998 | McCroskey | .......... | G01T 1/1642 250/363.02 |
| 6,242,743 B1 * | 6/2001 | DeVito | ................... | A61B 6/037 250/363.01 |
| 6,403,964 B1 | 6/2002 | Kyyhkynen | | |
| 6,448,544 B1 | 9/2002 | Stanton et al. | | |
| 6,483,107 B1 * | 11/2002 | Rabinovitz | .............. | G06F 1/181 250/239 |
| 6,587,538 B2 * | 7/2003 | Igarashi | ................... | A61B 6/06 250/367 |
| 6,590,214 B1 * | 7/2003 | Karmalawy | .......... | G01T 1/1648 250/363.01 |
| 6,693,291 B2 * | 2/2004 | Nelson | ................ | A61B 6/4233 250/363.01 |
| 7,009,183 B2 * | 3/2006 | Wainer | ................. | G01T 1/172 250/370.09 |
| 8,368,029 B2 * | 2/2013 | Wagenaar | ............ | G01R 33/481 250/370.12 |
| 8,824,635 B2 * | 9/2014 | Tkaczyk | ................. | A61B 6/037 250/363.08 |
| 9,116,216 B2 * | 8/2015 | Nalcioglu | ............ | G01R 33/481 |
| 9,134,440 B2 * | 9/2015 | Sanuki | ................. | G01T 1/2928 |
| 2002/0073717 A1 * | 6/2002 | Dean | ................... | G01R 33/34 62/50.7 |
| 2002/0130266 A1 | 9/2002 | Kyyhkynen | | |
| 2002/0188197 A1 * | 12/2002 | Bishop | ............... | A61B 5/02755 600/436 |
| 2003/0205676 A1 * | 11/2003 | Nelson | ................ | A61B 6/4233 250/370.09 |
| 2004/0026624 A1 * | 2/2004 | Wainer | ................ | G01T 1/172 250/370.09 |
| 2004/0104350 A1 * | 6/2004 | Tsuchiya | ............... | G01T 1/2928 250/370.08 |
| 2004/0129886 A1 * | 7/2004 | Lecoq | .................... | G01T 1/202 250/363.03 |
| 2004/0178348 A1 * | 9/2004 | Wainer | .................... | G01T 1/172 250/370.09 |
| 2004/0217293 A1 * | 11/2004 | Tsuchiya | ............... | G01T 1/2928 250/370.08 |
| 2005/0067573 A1 | 3/2005 | Albert et al. | | |
| 2005/0067579 A1 * | 3/2005 | Tsuchiya | ............... | G01T 1/2928 250/370.15 |
| 2006/0261281 A1 * | 11/2006 | Tsuchiya | ............... | G01T 1/2928 250/370.08 |
| 2008/0087833 A1 * | 4/2008 | McCroskey | ......... | A61B 5/0059 250/370.08 |
| 2008/0283760 A1 * | 11/2008 | Tsuchiya | ............... | G01T 1/2928 250/370.09 |
| 2009/0072159 A1 | 3/2009 | Yokoi et al. | | |
| 2009/0128867 A1 | 5/2009 | Edge | | |
| 2009/0242776 A1 * | 10/2009 | Kobashi | ................. | A61B 6/032 250/363.04 |
| 2010/0012846 A1 * | 1/2010 | Wang | .................... | G01T 1/1642 250/362 |
| 2010/0072377 A1 * | 3/2010 | Wagenaar | ........... | G01R 33/481 250/363.1 |
| 2011/0077511 A1 | 3/2011 | Kim et al. | | |
| 2011/0090633 A1 * | 4/2011 | Rabinovitz | ............. | G06F 1/184 361/679.31 |
| 2011/0168899 A1 * | 7/2011 | Cheshire | ............... | G01F 23/288 250/357.1 |
| 2011/0249879 A1 | 10/2011 | Wu et al. | | |
| 2011/0253901 A1 * | 10/2011 | Chmeissani Raad | ... | G01T 1/249 250/370.09 |
| 2012/0035465 A1 * | 2/2012 | Wagenaar | ............ | G01R 33/481 600/411 |
| 2013/0108019 A1 * | 5/2013 | Tkaczyk | ............... | G01T 1/247 378/62 |
| 2013/0264483 A1 * | 10/2013 | Abenaim | ............... | G01T 1/2018 250/363.01 |
| 2013/0266116 A1 * | 10/2013 | Abenaim | ............. | G01N 23/046 378/20 |
| 2013/0320234 A1 * | 12/2013 | Volokh | ................... | A61B 6/037 250/453.11 |
| 2014/0010426 A1 * | 1/2014 | Basu | ................... | G06T 11/005 382/131 |
| 2014/0313662 A1 * | 10/2014 | Aoki | ................... | G11B 33/126 361/679.39 |
| 2014/0361181 A1 * | 12/2014 | Liu | ........................ | G01T 1/1618 250/366 |
| 2016/0023019 A1 | 1/2016 | Filiberti et al. | | |
| 2016/0077216 A1 * | 3/2016 | Hefetz | ............... | H05K 7/20418 250/336.1 |
| 2016/0077217 A1 * | 3/2016 | Shahar | ................... | G01T 1/1648 250/362 |
| 2016/0095558 A1 * | 4/2016 | Choy | ................... | A61B 6/107 600/407 |
| 2016/0192530 A1 * | 6/2016 | Dunwoody | .......... | H05K 7/1487 361/679.48 |
| 2016/0282153 A1 * | 9/2016 | Hefetz | ................. | G01D 11/245 |
| 2017/0128750 A1 | 5/2017 | Filiberti et al. | | |
| 2017/0146372 A1 * | 5/2017 | Khen | ................... | G01D 11/245 |
| 2017/0285191 A1 * | 10/2017 | Hugg | ................... | G01T 1/249 |
| 2018/0059267 A1 * | 3/2018 | Ng | ........................ | G01T 1/161 |
| 2018/0095182 A1 * | 4/2018 | Su | ........................ | G01T 1/2985 |
| 2018/0106913 A1 * | 4/2018 | Jiang | ..................... | G01T 1/2985 |

\* cited by examiner

MODULAR GAMMA IMAGING DEVICE

BACKGROUND

Imaging devices perform many different functions such as medical imaging, security screening, image capture, or the like. The source of the imaging may be a radiological source, visible light, non-visible light, or any type of source for which the imaging device is capable of detection. For example, in a medical setting, a patient may be injected with a radiological agent and the imaging device may capture the emission of radiation from the patient's body for diagnostic analysis. As another example, in a security screening scenario, an individual's body or personal effect may be placed in an imaging device or scanner to search for prohibited materials. The imaging device may include a camera sensitive to the emission source, for example, a camera including a specific substance or object that is sensitive to or reacts to the emission source.

BRIEF SUMMARY

In summary, one aspect provides an imaging device, comprising: an enclosure comprising a casing and a radiation lining arranged within the casing to provide a radiation shield, wherein the enclosure comprises a removable portion; a plurality of modular components; each of the plurality of modular components comprising a plurality of gamma detectors including semiconductor crystals and being removable from the imaging device; the plurality of modular components being arranged such that the plurality of gamma detectors are configured in an array configuration with each of the plurality of gamma detectors having a predetermined spacing from each other gamma detector; a plurality of electronic communication components, wherein the plurality of electronic communication components facilitate communication from each of the gamma detectors to a processor using a hierarchical communication technique; and a cooling system.

Another aspect provides an imaging device, comprising: a plurality of electronic communication components facilitating hierarchical communication from a plurality of gamma detectors to a processor; the plurality of electronic communication components comprising a plurality of integrated circuits, a plurality of field programmable gate arrays, a plurality of array aggregators, a system control board, and the processor; wherein each gamma detector comprises one of the plurality of integrated circuits and wherein the gamma detectors are grouped into arrays; wherein each of the integrated circuits of the arrays communicate with one of the plurality of field programmable gate arrays assigned to the corresponding array and wherein the arrays of gamma detectors are grouped into units and wherein the units are grouped into drawers; wherein the field programmable gate arrays for a corresponding drawer communicate with one of the plurality of array aggregators assigned to the corresponding drawer; wherein the plurality of array aggregators communicate with the system control board and wherein the system control board communicates with the processor, the processor facilitating communication with a remote system.

A further aspect provides a gamma imaging device, comprising: a radiation-shielding enclosure comprising a casing and a lining comprising a lead alloy or tungsten alloy arranged within the casing to provide a complete radiation shield, wherein the enclosure comprises a top side, a bottom side, and four lateral sides, wherein one of the four lateral sides comprises a removable portion comprising a portion of the casing and a portion of the lining; a plurality of modular components; each of the plurality of modular components comprising a plurality of gamma detectors comprising semiconductor crystals and integrated circuits and being removable from the imaging device; the plurality of modular components being arranged such that the plurality of gamma detectors are configured in an array configuration with each of the plurality of gamma detectors having a predetermined spacing from each other gamma detector; a plurality of hierarchical electronic communication components facilitating communication from the plurality of gamma detectors to a processor; the plurality of electronic communication components comprising a plurality of integrated circuits, a plurality of field programmable gate arrays, a plurality of array aggregators, a system control board, and the processor; wherein each gamma detector comprises one of the plurality of integrated circuits and wherein the gamma detectors are grouped into arrays comprising twelve gamma detectors; wherein each of the integrated circuits of the arrays communicate with one of the plurality of field programmable gate arrays assigned to the corresponding array and wherein the arrays of gamma detectors are grouped into units comprising three arrays and wherein the units are grouped into drawers comprising four units, wherein the gamma imaging device comprises three drawers; wherein the field programmable gate arrays for a corresponding drawer communicate with one of the plurality of array aggregators assigned to the corresponding drawer; wherein the plurality of array aggregators communicate with the system control board and wherein the system control board communicates with the processor, the processor facilitating communication with a remote system; and a cooling system.

The foregoing is a summary and thus may contain simplifications, generalizations, and omissions of detail; consequently, those skilled in the art will appreciate that the summary is illustrative only and is not intended to be in any way limiting.

For a better understanding of the embodiments, together with other and further features and advantages thereof, reference is made to the following description, taken in conjunction with the accompanying drawings. The scope of the invention will be pointed out in the appended claims.

DETAILED DESCRIPTION

Figure 1:
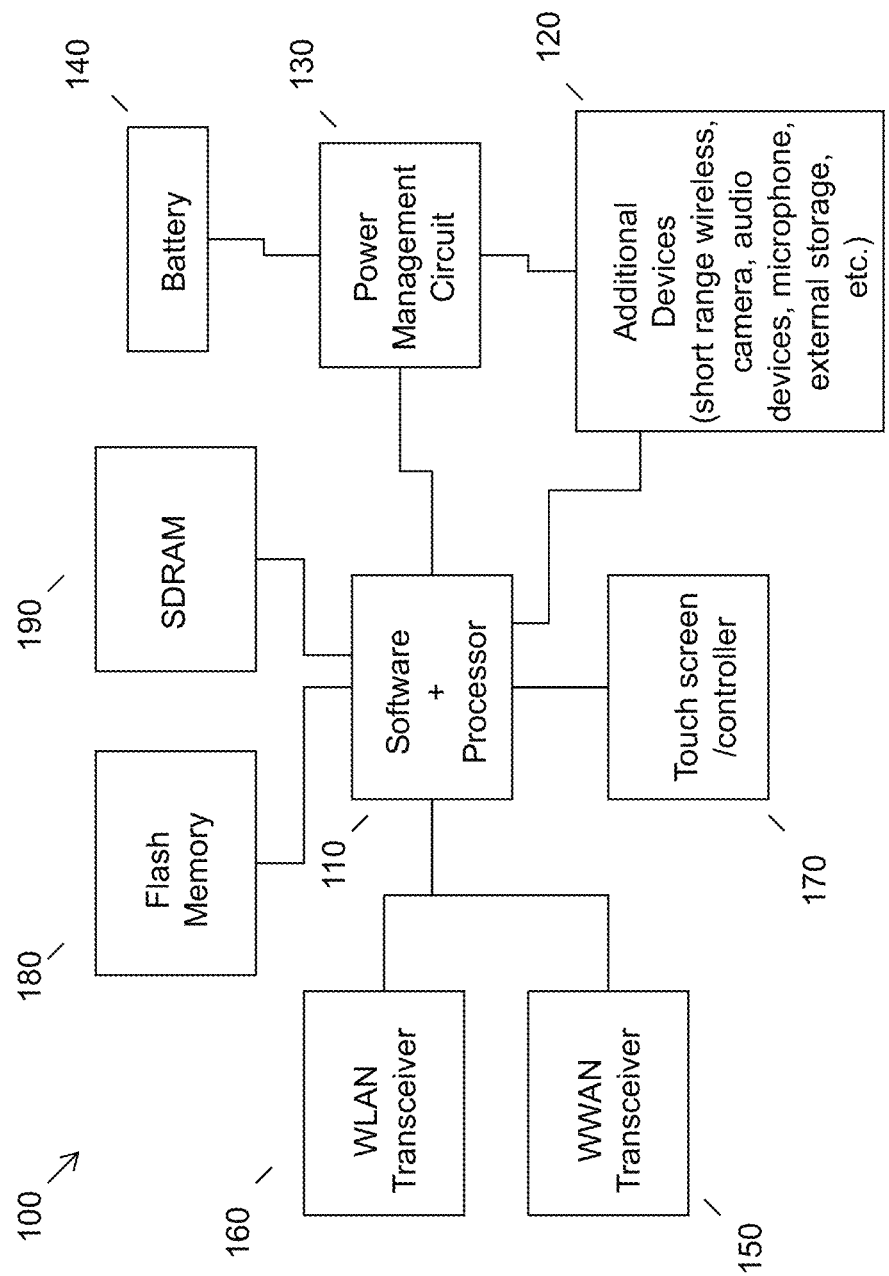
FIG. 1 illustrates an example of information handling device circuitry.

It will be readily understood that the components of the embodiments, as generally described and illustrated in the figures herein, may be arranged and designed in a wide variety of different configurations in addition to the described example embodiments. Thus, the following more detailed description of the example embodiments, as represented in the figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, the appearance of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, et cetera. In other instances, well known structures, materials, or operations are not shown or described in detail to avoid obfuscation.

Gamma imaging devices or cameras may be used to detect and take images of different people or objects. Gamma cameras are sensitive to and can detect gamma photons that may be emitted by radiological sources. For example, gamma cameras may be used in medical settings to view images of interior tissues of the human body. In such a setting the user may ingest, be injected with, or inhale radiopharmaceuticals that emit gamma photons. The gamma camera can then detect the gamma photons and provide an image that illustrates the location, energy, and concentration of the gamma photons. As another example, gamma cameras may be used in a security setting to detect and image gamma photons that are emitted by radioactive sources or astrophysical sources of x-rays and/or gamma photons.

The gamma camera includes crystals that are sensitive to the gamma photons. In an embodiment, when the gamma photon strikes the scintillator crystal it scintillates, which causes light to reach an array of photodetectors. The photodetectors then provide a signal indicating the location of the gamma photon interaction. In another embodiment, when the gamma photon strikes the semiconductor crystal it produces a charge cloud of electrons and holes which is collected by the cathode and pixelated anodes. The gamma camera then constructs an image from these signals which identifies the location of the emitted gamma photon within the imaged object. The image also provides a reader of the image with an idea of the concentration of the gamma photons. In the case of a medical setting, the medical professional can then determine a course of action based upon these images. In the case of a security setting, a security team can determine whether an object contains radiological material that may be a security threat using the image produced by the gamma camera.

Gamma cameras include many fragile parts, for example, the semiconductor crystals used to detect the gamma photons, sensitive electronic communication components paired with a specific crystal, and the like. In the case of breakdown or malfunction in the field, repairing the gamma camera can be difficult and may become costly due to the fragile parts. Additionally, because particular components are specifically paired with other components, more than one component may have to be replaced to ensure the replacement components are paired. For example, a single crystal may have an integrated circuit that is specifically paired to that crystal. The integrated circuit and crystal may be built and tested together during manufacture. Therefore, a different crystal cannot be paired with that integrated circuit and vice versa. Additionally, conventional gamma cameras are built such that a specific component can be replaced in the field. Since the crystal array is very fragile, replacing a single detector crystal may result in more damage and become a costly repair. Additionally, in the simplest design of large pixelated semiconductor detector gamma camera systems, the camera array is generally very large and heavy. Therefore, a technician generally cannot lift the camera without mechanical assistance. This can also result in more damage to the system as the camera is removed from its radiation-shielding enclosure using a mechanical lifting device and certain components are replaced.

Gamma cameras typically only have two access points, namely the top and bottom of the enclosure, because the enclosure is lined with a radiation shield. Accordingly, the gamma camera is designed such that only two pieces of the enclosure can be removed to access the components inside the device. Thus, in conventional gamma cameras, the only access to the inside of the camera is through the top of the device (the collimator side), or the enclosure lid, which is on the bottom of the device. Those skilled in the art will recognize that top and bottom are arbitrary labels, since the gamma camera can easily be flipped over to expose the previous underside. This means that to access components in the center of the device, a technician or other user may have to remove components surrounding the desired component.

Accordingly, an embodiment provides a gamma imaging device system that includes a modular construction that allows for removal of components within the device. The components within the camera are divided into modules that are removable by a single person without using mechanical assistance. Additionally, because the device allows removal of sections of components, for example, sections of the crystal array, the device is designed to ensure that tolerance between each of the components is maintained even after replacement of a section of a component. Additionally, the modules are designed such that fewer components have to be removed to access a malfunctioning component than in conventional gamma camera configurations. This assists in preventing additional damage that may be caused by the technician or other user during repair of the device.

In one embodiment, the removable portion of the imaging device is the front lateral side of the enclosure. This allows better access to the components within the device. The removable portion also includes a radiation-shielding lining portion, for example, a lead or tungsten alloy, such that when the removable portion is in place on the imaging device the device includes a radiation lining that provides a complete radiation shield.

Additionally, the device as described by embodiments herein includes an electronic communication system that communicates in a hierarchical fashion. Each of the gamma detectors within the device includes an integrated circuit. The gamma detectors are grouped into arrays of detectors with each of these arrays communicating with a field programmable gate array (FPGA). The arrays of gamma detectors are then grouped into units with the units being grouped into drawers. Each of the field programmable gate arrays within a drawer communicate with an array aggregator, with all the array aggregators communicating with a system control board. The system control board then communicates with a processor or single board computer which facilitates communication with a remote system, for example, the overall system that the imaging device is installed within, a cloud data storage system, and the like. Such a hierarchical electronic communication system allows for a reduction in the number of electronic communication components, thereby reducing the amount of heat generated by the system and the amount of processing that is required by the single board computer.

The illustrated example embodiments will be best understood by reference to the figures. The following description is intended only by way of example, and simply illustrates certain example embodiments.

While various other circuits, circuitry or components may be utilized in information handling devices, with regard to smart phone and/or tablet circuitry 100, an example illustrated in FIG. 1 includes a system on a chip design found for example in tablet or other mobile computing platforms. Software and processor(s) are combined in a single chip 110. Processors comprise internal arithmetic units, registers, cache memory, busses, I/O ports, etc., as is well known in the art. Internal busses and the like depend on different vendors, but essentially all the peripheral devices (120) may attach to a single chip 110. The circuitry 100 combines the processor, memory control, and I/O controller hub all into a single chip 110. Also, systems 100 of this type do not typically use SATA or PCI or LPC. Common interfaces, for example, include SDIO and I2C.

There are power management chip(s) 130, e.g., a battery management unit, BMU, which manage power as supplied, for example, via a rechargeable battery 140, which may be recharged by a connection to a power source (not shown). In at least one design, a single chip, such as 110, is used to supply BIOS like functionality and DRAM memory.

System 100 typically includes one or more of a WWAN transceiver 150 and a WLAN transceiver 160 for connecting to various networks, such as telecommunications networks and wireless Internet devices, e.g., access points. Additionally, devices 120 are commonly included, e.g., an image sensor such as a camera. System 100 often includes a touch screen 170 for data input and display/rendering. System 100 also typically includes various memory devices, for example flash memory 180 and SDRAM 190.

Figure 2:
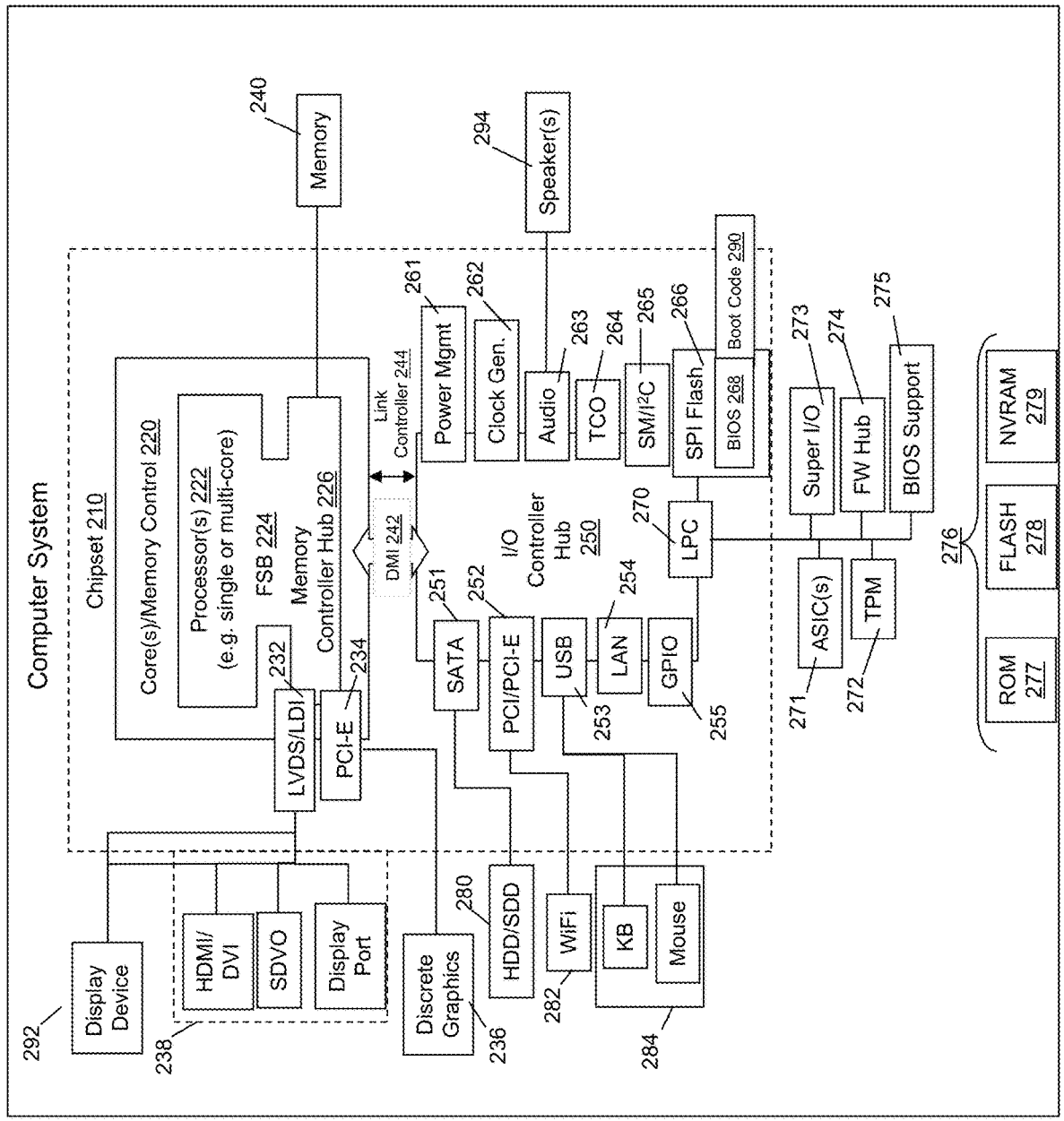
FIG. 2 illustrates another example of information handling device circuitry.

FIG. 2 depicts a block diagram of another example of information handling device circuits, circuitry or components. The example depicted in FIG. 2 may correspond to computing systems such as personal computers, laptop computers, or other devices. As is apparent from the description herein, embodiments may include other features or only some of the features of the example illustrated in FIG. 2.

The example of FIG. 2 includes a so-called chipset 210 (a group of integrated circuits, or chips, that work together, chipsets) with an architecture that may vary depending on manufacturer (for example, INTEL, AMD, ARM, etc.). INTEL is a registered trademark of Intel Corporation in the United States and other countries. AMD is a registered trademark of Advanced Micro Devices, Inc. in the United States and other countries. ARM is an unregistered trademark of ARM Holdings plc in the United States and other countries. The architecture of the chipset 210 includes a core and memory control group 220 and an I/O controller hub 250 that exchanges information (for example, data, signals, commands, etc.) via a direct management interface (DMI) 242 or a link controller 244. In FIG. 2, the DMI 242 is a chip-to-chip interface (sometimes referred to as being a link between a "northbridge" and a "southbridge"). The core and memory control group 220 include one or more processors 222 (for example, single or multi-core) and a memory controller hub 226 that exchange information via a front side bus (FSB) 224; noting that components of the group 220 may be integrated in a chip that supplants the conventional "northbridge" style architecture. One or more processors 222 comprise internal arithmetic units, registers, cache memory, busses, I/O ports, etc., as is well known in the art.

In FIG. 2, the memory controller hub 226 interfaces with memory 240 (for example, to provide support for a type of RAM that may be referred to as "system memory" or "memory"). The memory controller hub 226 further includes a low voltage differential signaling (LVDS) interface 232 for a display device 292 (for example, a CRT, a flat panel, touch screen, etc.). A block 238 includes some technologies that may be supported via the LVDS interface 232 (for example, serial digital video, HDMI/DVI, display port). The memory controller hub 226 also includes a PCI-express interface (PCI-E) 234 that may support discrete graphics 236.

In FIG. 2, the I/O hub controller 250 includes a SATA interface 251 (for example, for HDDs, SDDs, etc., 280), a PCI-E interface 252 (for example, for wireless connections 282), a USB interface 253 (for example, for devices 284 such as a digitizer, keyboard, mice, cameras, phones, microphones, storage, other connected devices, etc.), a network interface 254 (for example, LAN), a GPIO interface 255, a LPC interface 270 (for ASICs 271, a TPM 272, a super I/O 273, a firmware hub 274, BIOS support 275 as well as various types of memory 276 such as ROM 277, Flash 278, and NVRAM 279), a power management interface 261, a clock generator interface 262, an audio interface 263 (for example, for speakers 294), a TCO interface 264, a system management bus interface 265, and SPI Flash 266, which can include BIOS 268 and boot code 290. The I/O hub controller 250 may include gigabit Ethernet support.

The system, upon power on, may be configured to execute boot code 290 for the BIOS 268, as stored within the SPI Flash 266, and thereafter processes data under the control of one or more operating systems and application software (for example, stored in system memory 240). An operating system may be stored in any of a variety of locations and accessed, for example, according to instructions of the BIOS 268. As described herein, a device may include fewer or more features than shown in the system of FIG. 2.

Information handling device circuitry, as for example outlined in FIG. 1 or FIG. 2, may be used in devices such as tablets, smart phones, personal computer devices generally, and/or electronic devices which may be used in imaging devices or devices that may communicate with imaging devices. For example, the circuitry outlined in FIG. 1 may be implemented in a tablet or smart phone embodiment, whereas the circuitry outlined in FIG. 2 may be implemented in a personal computer embodiment.

Figure 3:
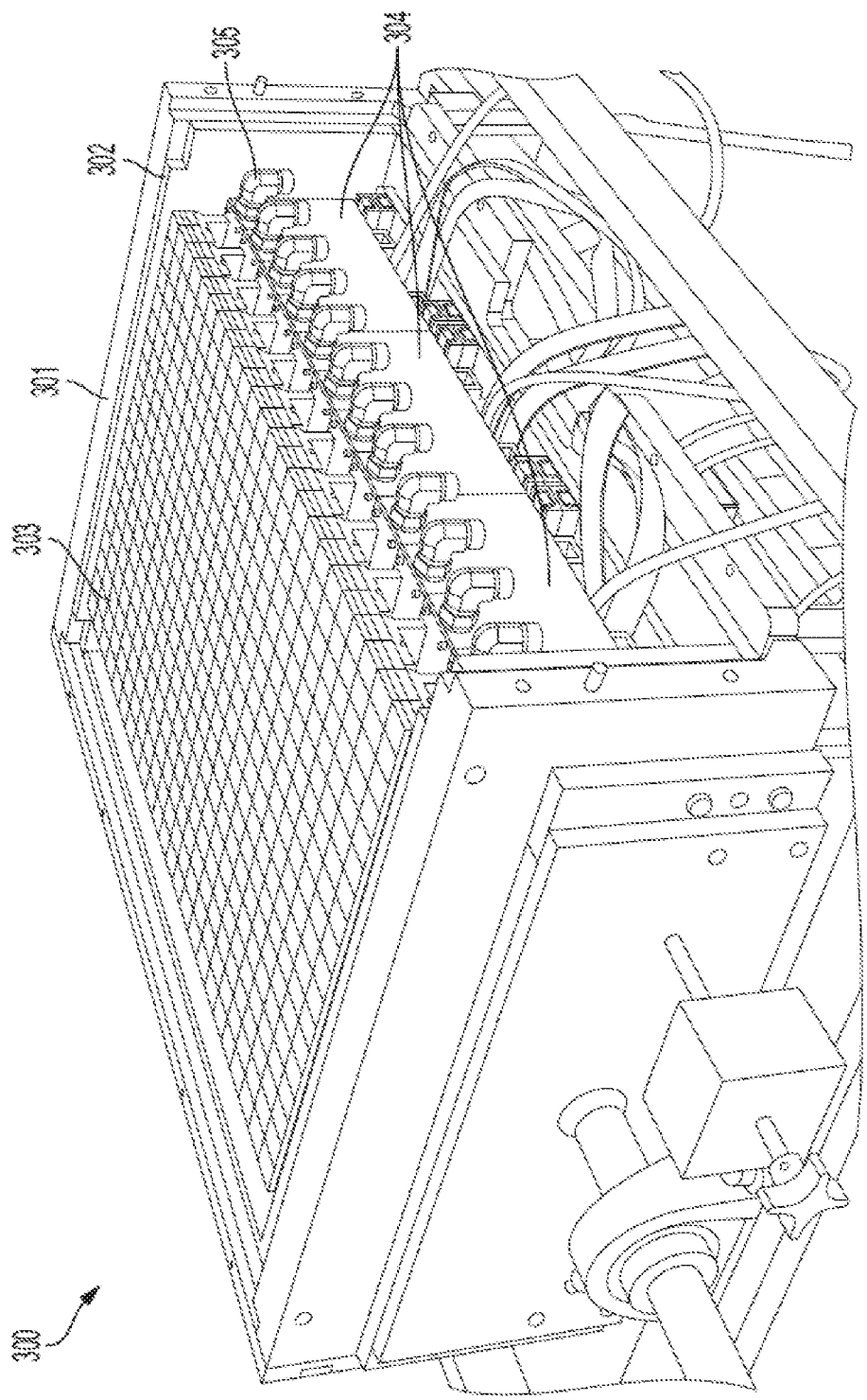
FIG. 3 illustrates an example modular gamma imaging device.

FIG. 3 illustrates an example modular gamma imaging device 300, also referred to herein as a gamma camera. The illustration in FIG. 3 shows the internals of the gamma camera. Therefore, the figure includes a removed top portion and side portion which would not be typically seen while in operation. The modular gamma camera 300 includes an enclosure having a top side, bottom side, and four lateral sides. The enclosure includes a casing 301 and a radiation lining 302. The casing and radiation lining can be seen in more detail in FIG. 4 where 401 is the casing and 402A and 402B make up a portion of the lining. The casing may be made of a lightweight but structurally strong material, for example, aluminum or the like. The radiation lining may be of any material that provides an acceptable level of radiation shielding and is generally lead or tungsten alloys. However, it should be understood that any radiation shield material may be used.

Figure 4:
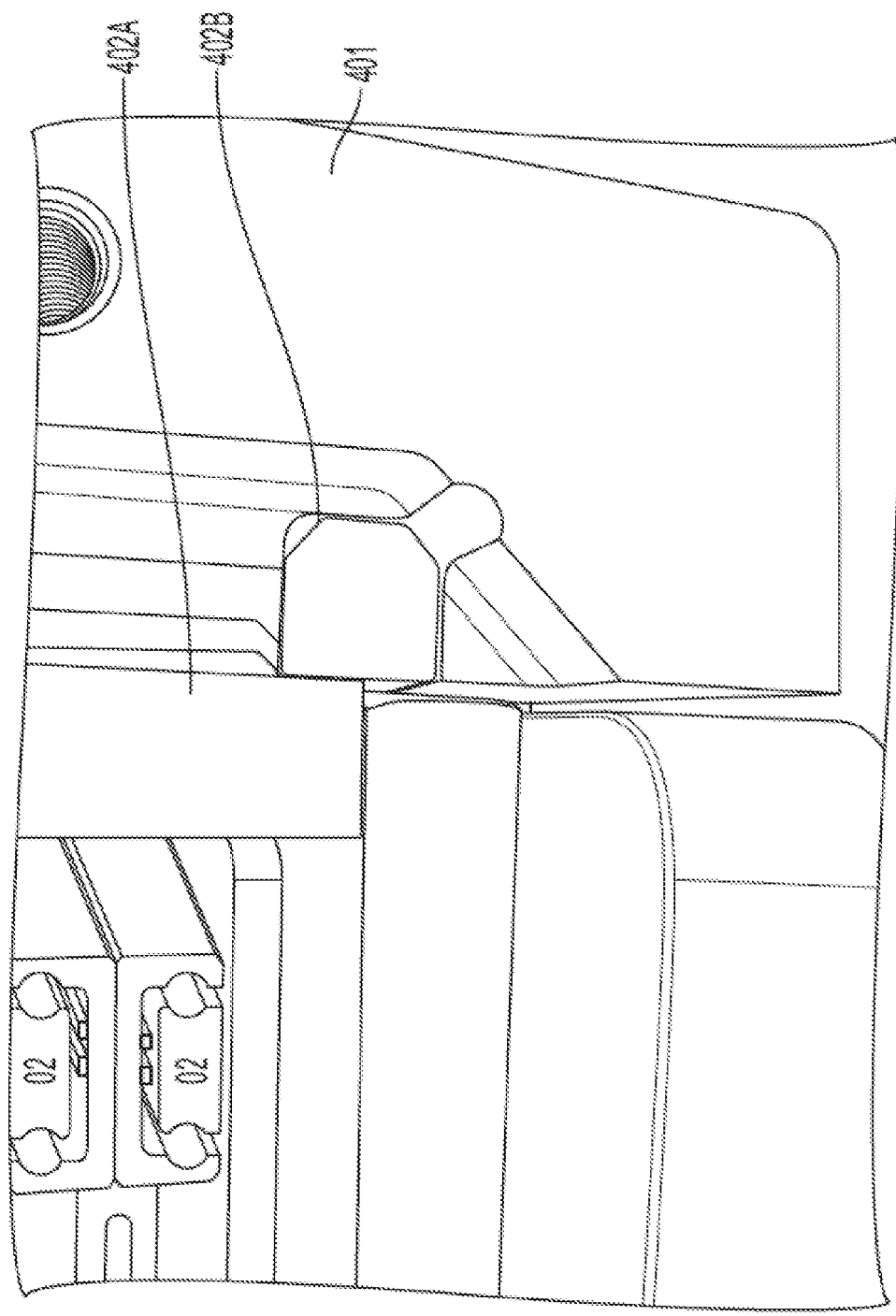
FIG. 4 illustrates an example radiation lining configuration.

The lining is arranged within the casing such that each portion of the camera has a sufficient thickness of lining to block most gamma photons of a particular energy (e.g., 365 keV, etc.), thereby creating a complete radiation shield. In order to accomplish this, the lining may be configured including multiple pieces. For example, as shown in FIG. 4, the lining includes plates 402A, for example the vertical and horizontal portions, and also includes lining strips 402B to cover the gap that is produced by the abutment of the plates 402A to each other. The arrangement of the lining within the casing may be referred to as a labyrinth arrangement.

Figure 5:
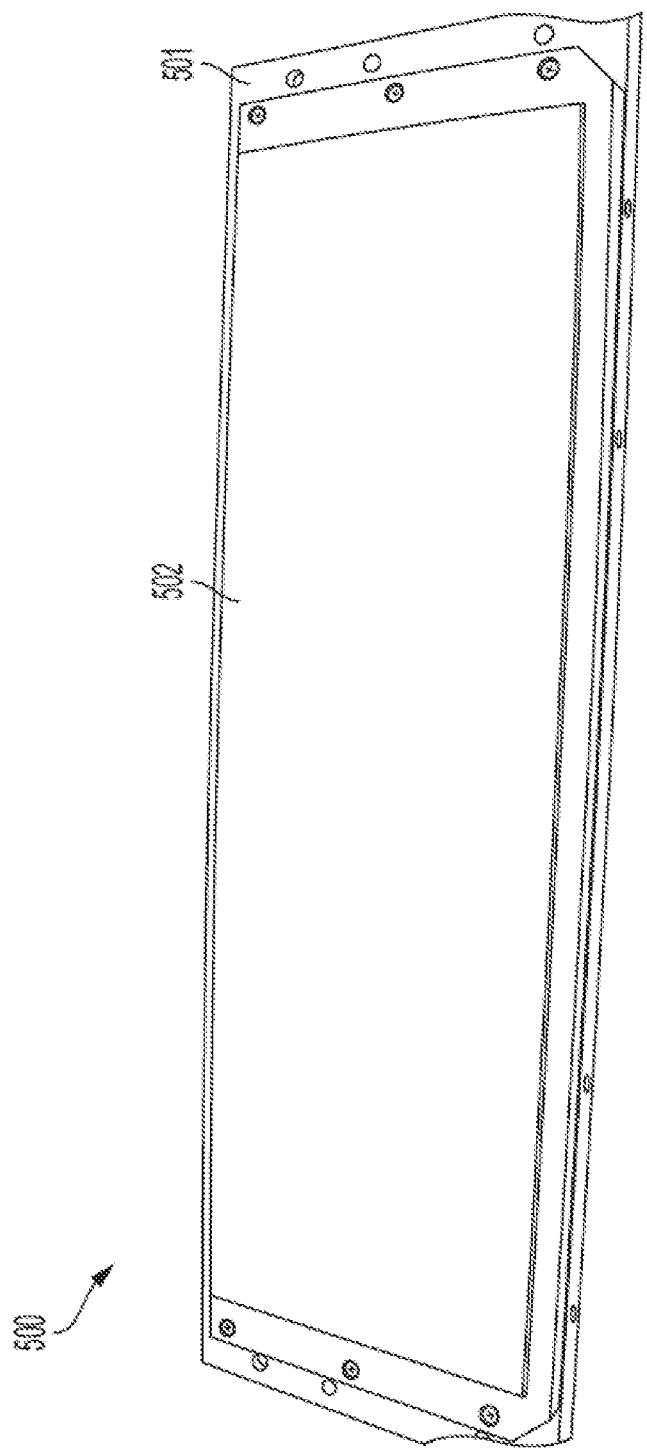
FIG. 5 illustrates an example removable cover including radiation shield.

The gamma camera enclosure also includes a removable portion as illustrated in FIG. 5. The removable portion of the gamma camera is one of the four lateral sides (preferably the front, for easiest access) instead of either the top or bottom as found in conventional gamma cameras. In FIG. 3, the removable portion would be attached at the front of the device (shown on the right side of FIG. 3). As shown in FIG. 5, the removable portion includes a portion of the casing 501 and also includes a portion of the lining 502. The lining is arranged within the casing such that when completely enclosed, the lining provides a complete radiation shield at all locations within the camera. Therefore, when the removable portion of the enclosure is installed, both the casing is complete and the radiation shield as provided by the lining is complete.

The gamma camera 300 also includes a plurality of modular components. The modular components are designed so that a field service technician or other user can remove particular modules in the field, not only without assistance, but also in such a manner to reduce the possibility of damage to other components. The gamma camera may include a plurality of gamma detectors 303 including a semiconductor crystal, for example, a cadmium-zinc-telluride (CdZnTe or CZT) or cadmium-telluride (CdTe) crystal. The gamma detectors may also include an integrated circuit, for example, an application-specific integrated circuit (ASIC). The integrated circuit may be paired with the crystal, for example, built and tested with a specific crystal. Therefore, the integrated circuit and crystal may be treated as a single unit, referred to as a gamma module or gamma detector. The term gamma detector will be used herein throughout for ease of readability, but other terms may be used and known in the field.

The pixelated gamma detectors may be designed in an array configuration, for example, as seen in FIG. 3. In this embodiment, the CZT pixelated gamma detectors are 22 mm×22 mm and 5 mm thick with 11×11 pixels on a 2.0 mm pitch. The array size shown is 18×24 gamma detectors with size 396 mm×528 mm. In order to perform properly and provide a high resolution, each of the gamma detectors may be installed within the gamma camera having a specific spacing between the detector pixels, or more specifically, between the crystals of the detectors. In practice, this spacing may be a very small gap, for example, half of a millimeter with a tolerance value. The pixel pitch is maintained across the array by making the edge pixels slightly smaller, so that a small air gap can be maintained between detector crystals. Due to tight spacing between the detectors and the fragility of the crystals, removing a detector may easily result in damage (e.g., chipping, cracking, etc.) to more than one of the crystals. Accordingly, the system as disclosed herein is designed to minimize the possibility of damage to other components while allowing removal and replacement of certain modules. Additionally, the system is designed in order to maintain the spacing between the crystals even if after modules are replaced.

While each gamma detector may ultimately be removable from the gamma camera, in the field this is undesirable due to the fragility of the crystals of the gamma detector. Accordingly, the gamma camera as described herein groups the gamma detectors into modules and drawers. First, the gamma detectors are grouped into arrays of twelve gamma detectors, based in part upon the choice of FPGA capable of servicing the signals from this size array. Depending on the electronic communication components, the gamma detectors may be grouped into larger or smaller groups in different applications. The array of twelve gamma detectors may be a two detector by six detector array, referred to as a 2×6 array. Three of these 2×6 arrays may then be grouped into modules of thirty-six detectors, for example, as a two-by-eighteen detector array, also called a 2×18 column. In the system as described herein, the 2×18 columns or 2×6 arrays may be removable from the system by a field service engineer, technician, or other user. Accordingly, the 2×18 column may include any and all electronic communication components that are unique to that module. The module and mating component may include communication or mating connections that allow for snapping in the module, rather than having to manually connect cables or wires that could result in miswiring or damage to a module or component.

In order to more easily remove the 2×18 column modules, the modules may be grouped into drawers, each drawer including four column modules. The drawers, as explained in more detail below, allow the modules to be moved out of the gamma camera enclosure in order to more easily access the module and to minimize the possibility of damage to other modules that may be functioning correctly. Since each drawer contains four modules, the most modules that have to be removed to access a failed or malfunctioning component is two modules. For example, if the target module (i.e., the module that is intended to be removed) is one of the modules on the outside of the drawer, then only that module needs to be removed. If the target module is in the middle of the drawer, one of the modules on the outside needs removed and then the interior target module, in this example, can be removed. Since at the most only two column modules need to be removed this minimizes the risk of damage to other modules.

The gamma camera 300 is designed with three modular drawers 304 that can be moved in and out of the imaging device via a mechanical mechanism. The term "drawer" will be used herein throughout. However, this is used as a term to describe the movement of the module as opposed to the construction of the module. In other words, each module may not include four sides and a bottom as found on a standard cabinet drawer. The drawers are mounted on a slidable mechanism (e.g., drawer slides, linear slides, carriage slides, etc.) that may have one or more slidable components. For example, the slidable mechanism may include two slides, one on each side of the module, one slide on the bottom of the module or the like. The slidable mechanism provides a mechanism so that the drawer may be moved parallel to a bottom plane of the imaging device. In other words, the drawers move out of the imaging device through a lateral side of the imaging device. The slidable mechanisms may be installed on one or more sides of the drawer module, the bottom of the drawer module, or a combination thereof. When the drawers are moved out from the gamma camera, the modules as installed on the drawers are cantilevered from the imaging device. Therefore, the drawer slides are designed to withstand bending and torsion that can result from being in a cantilevered position for an extended period of time.

Additionally, since the crystal arrays have a predetermined gap tolerance between each of the detectors the slidable mechanisms are designed such that the gap tolerance and/or alignment of the drawer is maintained when the drawer is moved out from the device and then moved back into within the imaging device. Also, to assist in maintaining the correct gap and tolerance, the drawers and/or drawer slides may be adjustable so that the drawers can be moved to the correct position. Mechanical gap indicators may be used to help set and verify the proper gap.

When the drawer is in place within the device, a mechanical stop block is used to prevent the drawer from moving within the enclosure. The mechanical stop block may be a part of the slidable mechanism, for example, as a lock or stop on the slidable mechanism. Alternatively, the stop block may be a separate piece that is put into place when the drawer is in position within the enclosure, for example, a bolt, object that is attached to the slidable mechanism or drawer, or the like, which may hold the drawer into position even when the gamma camera is moved. Additionally, the stop block may act to keep the drawer in position so that the gap tolerance between detectors is maintained. Additionally, the crystal array may be sensitive to a crystal being out of line, for example, in the X direction, in the Y direction, or the like. Therefore, the stop block may be used to maintain the position of the drawer in the X and/or Y direction.

The gamma camera 300 may also include a cooling system in order to remove heat from the system. Heat may be generated by various electronic communication components, most notably the ASICs and FPGAs. As shown in FIG. 3, the cooling system may include a liquid cooling system 305. However, the cooling system may be a different type of cooling system as used in different systems for thermal cooling. For example, the cooling system may include a liquid cooling system (e.g., water, glycol, etc.), forced air cooling system where air is forced into the system thereby causing the warm air to be forced out of the system, passive air cooling system where air circulates through the system based upon thermal dynamic principles, or any other type of cooling system. Depending on the cooling system, the gamma camera may include different components. For example, in the liquid cooled system as shown in FIG. 3, the cooling system includes piping, valves, pumps, radiators and other components, to ensure that the liquid does not come into contact with the other components, for example, electronic communication components, but still allows cooling of the entire device.

The gamma camera includes an electronic communication system that facilitates communication from each of the gamma detectors to a remote system. Generally, two types of communications are utilized: control and data, which may be passed on two separate communication busses. The electronic communication system may include a plurality of integrated circuits, a plurality of field programmable gate arrays (FPGAs), a plurality of array aggregators, which may comprise FPGAs, a system control board, which also may comprise an FPGA, and a processor or single board computer. Different hardware components that perform the same function may be used rather than the ones specifically mentioned here. The number of hierarchical layers may vary based upon the size of the detector array and the selection of components, such as the FPGAs. Each of the electronic communication components may be designed to perform a specific function. For example, the ASICs may be specifically programmed to be paired with a particular crystal as part of the gamma detector. Each of the FPGAs may be used within a specific position on the communication hierarchy, as described in more detail below, and, therefore, may be programmed to perform that function with expectations that it will send and receive communications from an electronic communication component of a lower level as well as an electronic communication component of a higher level.

The system as described herein has been designed such that the firmware for each of the FPGAs can be updated or upgraded in the field without having to open the enclosure of the imaging device to access an individual FPGA. A technician or other user can connect to the device through a communication port, for example, an Ethernet connection, universal serial bus (USB) connection, or the like, and feed a firmware image or upgrade to the FPGA. Alternatively, an upgrade may be pushed to the imaging device through a remote system. For example, a technician or other user may access the camera through a remote system, for example, through a network connection, through a web browser, or the like, and provide the camera instructions for upgrading the firmware stored on the camera. Such an upgrade system is referred to as "pushing" upgrades, for example, mobile phones and other mobile devices receive firmware upgrades in such a fashion.

Additionally, the technician or other user can provide an upgrade to a specific FPGA. In other words, the technician or other user can identify a particular FPGA for upgrade and upgrade that particular FPGA without changing the state of other FPGAs in the system. Each FPGA also includes a so-called "golden image" in the event that a firmware upgrade causes a malfunction or improperly loads. In the case that the system detects a problem with the firmware, the system can automatically load the golden image back onto the FPGA so that the entire imaging device can operate properly without requiring a technician to service the device. The system also includes safeguards so that an image intended for one FPGA cannot be loaded on a different FPGA. The system will recognize the image as belonging to one FPGA and will reject that image if there is an attempt to load it onto a different FPGA.

The electronic communication system of the gamma camera may be a hierarchical communication system. In such a system more than one electronic communication component associated with a small hardware component of the subsystem may communicate with one of a plurality of electronic communication components, which, in turn, communicate with another electronic communication component. In other words, the electronic communication system may be broken down into hierarchies where an electronic communication component at the top of the hierarchy communicates with more than one electronic communication component of the hierarchical step down, in which each of the electronic communication components of that hierarchical step communicate with multiple electronic communication components of the next step down, and so on. As another way to describe this communication path, the system may contain hundreds of detectors, each having an electronic communication component for communication. These detectors may be grouped so that a plurality communicate with one of a plurality of electronic communication components. These electronic communication components may then be grouped so that a plurality of them communicate with another level of electronic communication components, and so on until only a single electronic communication component communicates with a remote system.

As a practical explanation, as discussed above, each of the gamma detectors includes an application-specific integrated circuit (ASIC). The gamma detectors are grouped into 2×6 arrays of twelve detectors. Each of these arrays of twelve detectors may communicate with an FPGA that is assigned to the array. Specifically, the integrated circuit of each of the gamma detectors may communicate with an FPGA associated or assigned to that array. Three of these 2×6 arrays may be grouped as a 2×18 column module of thirty-six gamma detectors, where this column module includes three FPGAs. The column modules are then grouped as three drawers that each include four column modules. The four array 2×18 column modules within a drawer, comprising the twelve FPGAs that are associated with the 2×6 arrays, then communicate with an array aggregator board assigned to or otherwise associated with the drawer. The three array aggregators associated with the three drawers then communicate with a system control board that communicates with a processor or single board computer. The processor or single board computer facilitates communication to a remote system.

Each of the array aggregator boards and the system control board comprise an FPGA. In the described embodiment, there are 36 FPGAs at the 2×6 array level, 3 FPGAs at the array aggregator board level, and 1 FPGA at the system control board level. There is also a system on a chip (SoC) processor on the system control board that communicates with the host computer through an application programming interface (API) software program. The SoC includes a plurality of processor cores that may be used for data manipulation, although this may also be performed in the API or in higher level software on the host computer.

Such a hierarchical communication structure allows the count rate of the overall imaging device to be higher than in conventional imaging devices. The hierarchical communication structure reduces the amount of processing that must occur at the end-point communication node. In other words, at each of the communication node points (e.g., integrated circuit, FPGA, array aggregator, system control board, etc.) the information provided into that node is distilled down into the information necessary for the next component to perform its function. Therefore, by the time that the information reaches the last communication node, the information has been distilled into only the necessary information, thereby reducing the amount of information that has to be output to the remote system. Thus, the count rate of the system as described herein can be much higher than the count rate of conventional imaging device systems. In fact, a traditional gamma camera, with a monolithic scintillator crystal and an array of photodetectors, is paralyzed while the readout electronic communication components process a single gamma photon event. Such traditional cameras may be limited to 300 thousand events per second or less. A pixelated array of semiconductor detectors with a hierarchical readout architecture, as described herein, consist of hundreds of independent small area gamma cameras. Such a system may only be paralyzable at the pixel level and so is capable of count rates of a million events per second or greater.

Additionally, the hierarchical digital camera reduces the total number of data packets that must be sent to the host computer by creating a custom communication packet which is more efficient than a conventional gamma camera. When the digital camera receives communications that are intended to be sent or transmitted to the remote host computer, the camera packages the packets in sizes that are optimized for transmission through the communication channel. Rather than sending individually every data communication that is received by the camera to the remote computer system, the camera readout electronic communication components will collect the data communications and will package the data into a single packet. The system then waits until a communication packet is full, has been optimized, or a sufficient time has passed (slow event rate or end of acquisition, for example) before sending the communication to the remote system. This reduces the number of communication packets that have to be sent to the remote computer system.

Additionally, because the amount of information that is provided to a remote computer system is less than in conventional systems, the connection to the remote system can be a simple plug-in communication channel, for example, a gigabit Ethernet connection, a universal serial bus (USB) connection, and the like. This plug-in communication channel also assists in increasing the count rate as opposed to frame grabbers or optical communication connections as used in conventional imaging device systems.

Figure 6:
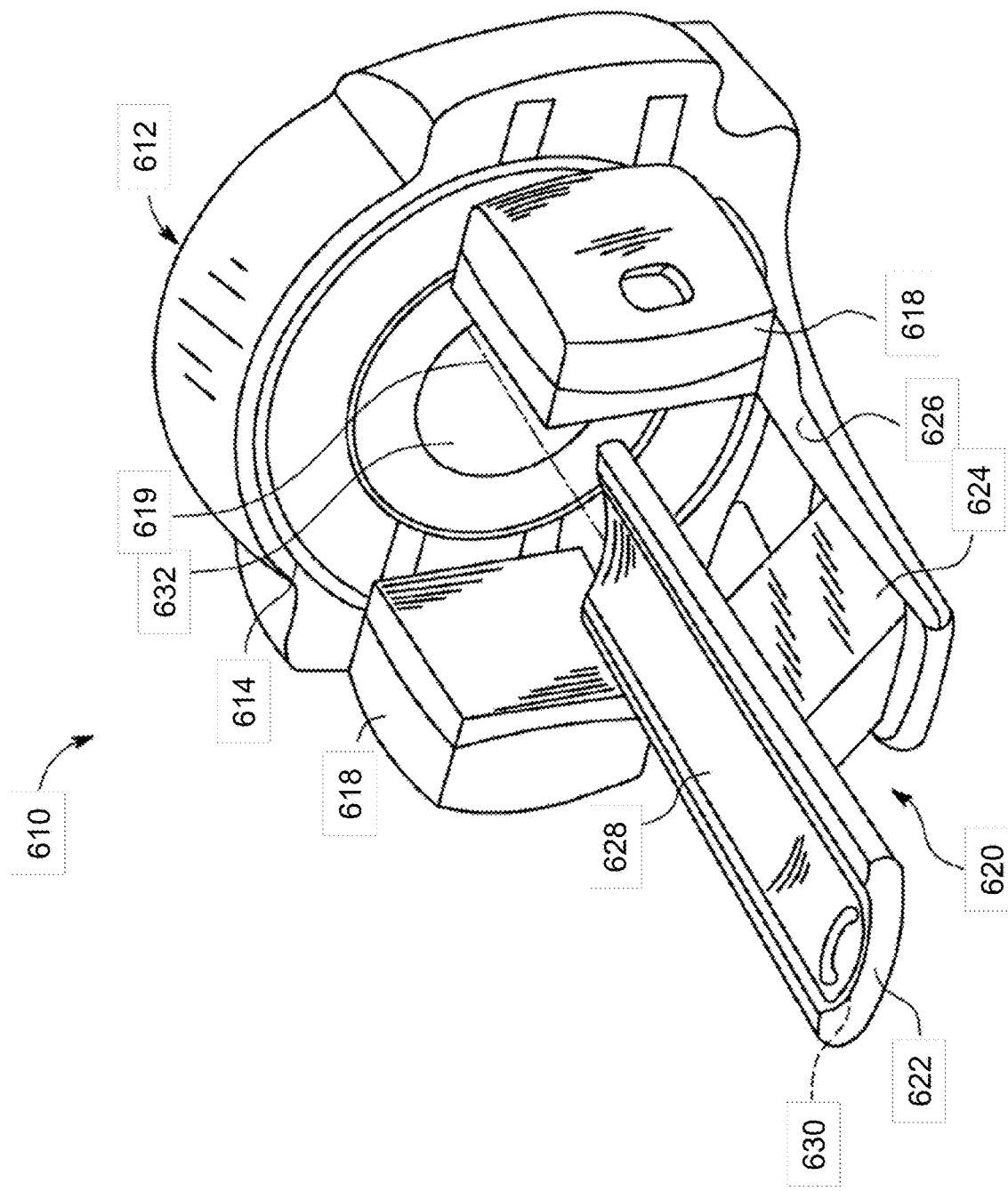
FIG. 6 illustrates another embodiment of an imaging device that may use the disclosed embodiments.

Referring now to FIG. 6, the pixelated detectors and/or gamma cameras of the various embodiments may be provided as part of different types of imaging systems, for example, nuclear medicine (NM) imaging systems such as positron emission tomography (PET) imaging systems, single-photon emission computed tomography (SPECT) imaging systems and/or x-ray imaging systems and x-ray computed tomography (CT) imaging systems, among others. For example, FIG. 6 is a perspective view of an exemplary embodiment of a medical imaging system 610 constructed in accordance with various embodiments, which in this embodiment is a SPECT imaging system. The system 610 includes an integrated gantry 612 that further includes a rotor 614 oriented about a gantry central bore 632. The rotor 614 is configured to support one or more NM pixelated cameras 618 (two cameras 618 are shown), such as, but not limited to gamma cameras, SPECT detectors, multi-layer pixelated cameras (e.g., Compton camera) and/or PET detectors. It should be noted that when the medical imaging system 610 includes a CT camera or an x-ray camera, the medical imaging system 610 also includes an x-ray tube (not shown) for emitting x-ray radiation towards the detectors. In various embodiments, the cameras 618 are formed from pixelated detectors as described in more detail herein. The rotors 614 are further configured to rotate axially about an examination axis 519.

A patient table 620 may include a bed 622 slidingly coupled to a bed support system 624, which may be coupled directly to a floor or may be coupled to the gantry 612 through a base 626 coupled to the gantry 612. The bed 622 may include a stretcher 628 slidingly coupled to an upper surface 630 of the bed 622. The patient table 620 is configured to facilitate ingress and egress of a patient (not shown) into an examination position that is substantially aligned with examination axis 619. During an imaging scan, the patient table 620 may be controlled to move the bed 622 and/or stretcher 628 axially into and out of a bore 632. The operation and control of the imaging system 610 may be performed in any manner known in the art. It should be noted that the various embodiments may be implemented in connection with imaging systems that include rotating gantries or stationary gantries.

Figure 7:
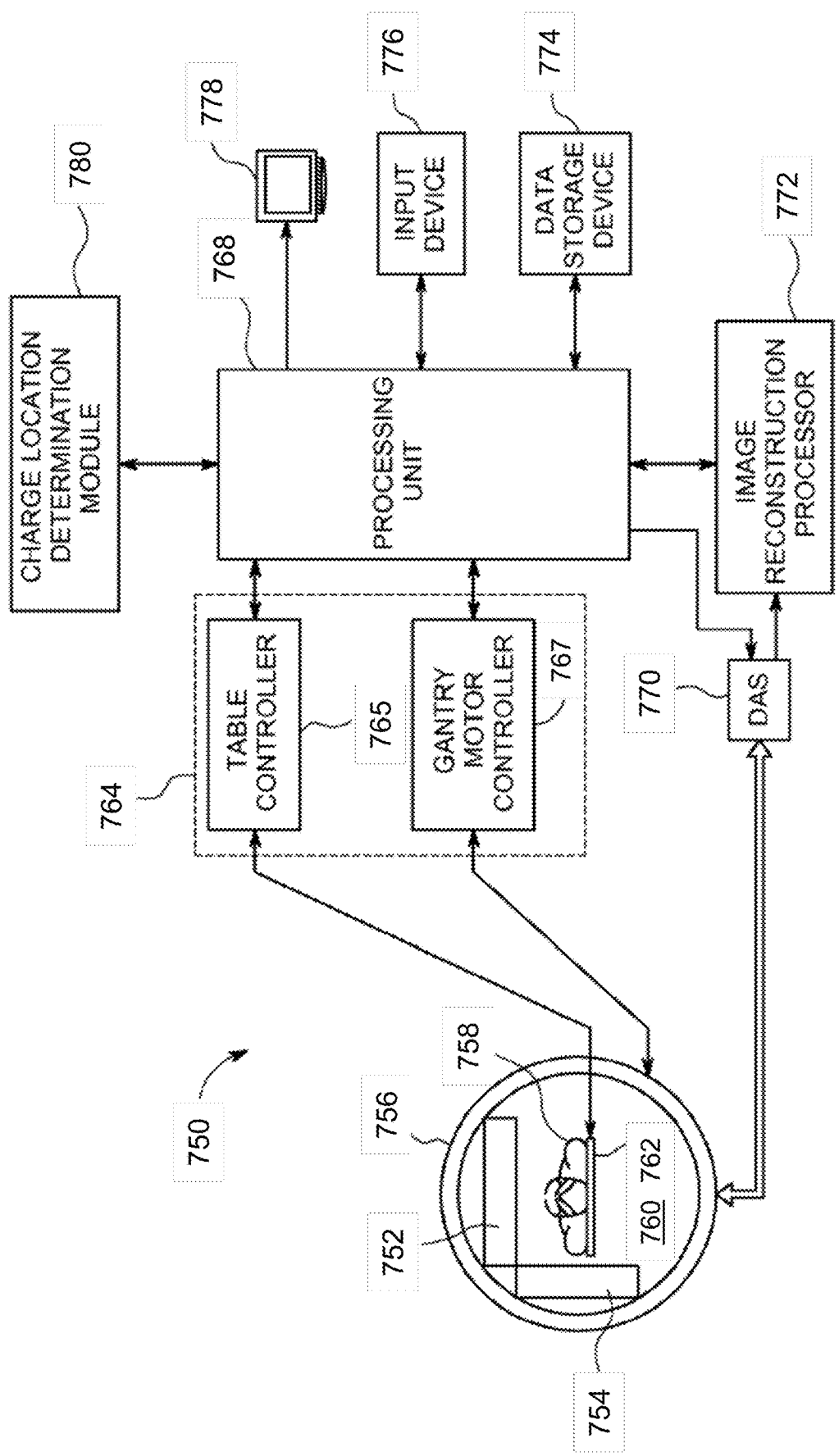
FIG. 7 illustrates a further example of information handling device circuitry.

Referring now to FIG. 7, which illustrates a block diagram illustrating an imaging system 750 that has a plurality of pixelated imaging detectors and/or gamma cameras configured in accordance with various embodiments mounted on a gantry. It should be noted that the imaging system may also be a multi-modality imaging system, such as an NM/CT imaging system. The imaging system 750, illustrated as a SPECT imaging system, generally includes a plurality of pixelated imaging detectors 752 and 754 (two are illustrated)

mounted on a gantry 756. It should be noted that additional imaging detectors may be provided. The imaging detectors 752 and 754 are located at multiple positions (e.g., in an L-mode configuration, as shown) with respect to a patient 758 in a bore 760 of the gantry 756. The patient 758 is supported on a patient table 762 such that radiation or imaging data specific to a structure of interest (e.g., the heart) within the patient 758 may be acquired. It should be noted that although the imaging detectors 752 and 754 are configured for movable operation (azimuthally around, radially in or out, rotatably around an axis, tiltably about a pivot, and the like) of the gantry 756, in some imaging systems, imaging detectors are fixedly coupled to the gantry 756 and in a stationary position, for example, in a PET imaging system (e.g., a ring of imaging detectors). It also should be noted that the imaging detectors 752 and 754 may be formed from different materials as described herein and provided in different configurations known in the art, such as flat or curved panels.

One or more collimators may be provided in front of the radiation detection face (not shown) of one or more of the imaging detectors 752 and 754. The imaging detectors 752 and 754 acquire a 2D image that may be defined by the x and y location of a pixel and the location of the imaging detectors 752 and 754. The radiation detection face (not shown) is directed towards, for example, the patient 758, which may be a human patient, animal, airport baggage, or the like.

A controller unit 764 may control the movement and positioning of the patient table: 762 with respect to the imaging detectors 752 and 754 and the movement and positioning of the imaging detectors 752 and 754 with respect to the patient 758 to position the desired anatomy of the patient 758 within the fields of view (FOVs) of the imaging detectors 752 and 754, which may be performed prior to acquiring an image of the anatomy of interest. The controller unit 764 may have a table controller 765 and a gantry motor controller 767 that each may be automatically commanded by a processing unit 768, manually controlled by an operator, or a combination thereof. The table controller 765 may move the patient table 762 to position the patient 758 relative to the FOV of the imaging detectors 752 and 754. Additionally, or optionally, the imaging detectors 752 and 754 may be moved, positioned or oriented relative to the patient 758 or rotated about the patient 758 under the control of the gantry motor controller 767.

The imaging data may be combined and reconstructed into an image, which may comprise 2D images, a 3D volume or a 3D volume over time (4D).

A Data Acquisition System (DAS) 770 receives analog and/or digital electrical signal data produced by the imaging detectors 752 and 754 and decodes the data for subsequent processing as described in more detail herein. An image reconstruction processor 772 receives the data from the DAS 770 and reconstructs an image using any reconstruction process known in the art. A data storage device 774 may be provided to store data from the DAS 770 or reconstructed image data. An input device 776 also may be provided to receive user inputs and a display 778 may be provided to display reconstructed images. A charge location determination module 780 may provide x and y position for each gamma photon interaction with the pixelated imaging detectors 752 and 754. In an embodiment, a depth-of-interaction z position may be determined.

Such a system provides a technical improvement over conventional gamma imaging devices. Using the system as described herein, the imaging device can be worked on in the field while reducing the possibility of damage to other components. Additionally, the system as described herein provides a hierarchical communication system that allows for efficient communications and reduction of hardware components.

As will be appreciated by one skilled in the art, various aspects may be embodied as a system, method or device program product. Accordingly, aspects may take the form of an entirely hardware embodiment or an embodiment including software that may all generally be referred to herein as a "circuit," "module" or "system." Furthermore, aspects may take the form of a device program product embodied in one or more device readable medium(s) having device readable program code embodied therewith.

It should be noted that the various functions described herein may be implemented using instructions stored on a device readable storage medium such as a non-signal storage device that are executed by a processor. A storage device may be, for example, an electronic, magnetic, optical, electromagnetic, infrared, or semiconductor system, apparatus, or device, or any suitable combination of the foregoing. More specific examples of a storage medium would include the following: a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a storage device is not a signal and "non-transitory" includes all media except signal media.

Program code embodied on a storage medium may be transmitted using any appropriate medium, including but not limited to wireless, wireline, optical fiber cable, RF, et cetera, or any suitable combination of the foregoing.

Program code for carrying out operations may be written in any combination of one or more programming languages. The program code may execute entirely on a single device, partly on a single device, as a stand-alone software package, partly on single device and partly on another device, or entirely on the other device. In some cases, the devices may be connected through any type of connection or network, including a local area network (LAN) or a wide area network (WAN), or the connection may be made through other devices (for example, through the Internet using an Internet Service Provider), through wireless connections, e.g., near-field communication, or through a hard wire connection, such as over a USB connection.

Example embodiments are described herein with reference to the figures, which illustrate example methods, devices and program products according to various example embodiments. It will be understood that the actions and functionality may be implemented at least in part by program instructions. These program instructions may be provided to a processor of a device, a special purpose information handling device, or other programmable data processing device to produce a machine, such that the instructions, which execute via a processor of the device implement the functions/acts specified.

It is worth noting that while specific blocks are used in the figures, and a particular ordering of blocks has been illustrated, these are non-limiting examples. In certain contexts, two or more blocks may be combined, a block may be split into two or more blocks, or certain blocks may be re-ordered or re-organized as appropriate, as the explicit illustrated examples are used only for descriptive purposes and are not to be construed as limiting.

As used herein, the singular "a" and "an" may be construed as including the plural "one or more" unless clearly indicated otherwise.

This disclosure has been presented for purposes of illustration and description but is not intended to be exhaustive or limiting. Many modifications and variations will be apparent to those of ordinary skill in the art. The example embodiments were chosen and described in order to explain principles and practical application, and to enable others of ordinary skill in the art to understand the disclosure for various embodiments with various modifications as are suited to the particular use contemplated.

Thus, although illustrative example embodiments have been described herein with reference to the accompanying figures, it is to be understood that this description is not limiting and that various other changes and modifications may be affected therein by one skilled in the art without departing from the scope or spirit of the disclosure.

What is claimed is:

1. An imaging device, comprising:
   an enclosure comprising a casing and a radiation lining arranged within the casing to provide a radiation shield, wherein the enclosure comprises a removable portion;
   a plurality of modular components;
   each of the plurality of modular components comprising a plurality of gamma detector elements including semiconductor crystals and being removable from the imaging device, wherein the plurality of gamma detector elements comprises a subset of the gamma detector elements of the imaging device;
   the plurality of modular components being arranged such that the plurality of gamma detector elements are configured in an array configuration with each of the plurality of gamma detector elements having a predetermined spacing from each other gamma detector element wherein each of the plurality of modular components corresponds to one of a plurality of drawers and each of the plurality of drawers are mounted on a slideable mechanism, wherein each of the drawers is parallel to a bottom plane of the imaging device, wherein each of the plurality of modular components are field serviceable while maintaining the predetermined spacing between each of the gamma detector elements through travel of a corresponding drawer between a locked-closed position and a cantilevered position and wherein the predetermined spacing facilitates high resolution images across the plurality of modular components;
   a plurality of electronic communication components, wherein the plurality of electronic communication components facilitate communication from each of the gamma detector elements to a processor using a hierarchical communication technique; and
   a cooling system.

2. The imaging device of claim 1, wherein the imaging device comprises a gamma camera.

3. The imaging device of claim 1, wherein the plurality of semiconductor crystals comprises a plurality of cadmium-zinc-telluride (CdZnTe or CZT) or cadmium-telluride (CdTe) crystals.

4. The imaging device of claim 1, wherein the enclosure comprises a top side, a bottom side, and four lateral sides and wherein the removable portion comprises one of the four lateral sides.

5. The imaging device of claim 1, wherein the plurality of modular components are grouped into a drawer and wherein the drawer comprises a slideable mechanism allowing the drawer of modular components to move parallel to a side of the enclosure.

6. The imaging device of claim 5, wherein the drawer comprises a mechanical stop block that, when in operation, prevents movement of the slideable mechanism.

7. The imaging device of claim 1, wherein the modular components comprise a plurality of gamma detector elements grouped as a module and a plurality of electronic communication components.

8. The imaging device of claim 7, wherein each of the electronic communication components is assigned to a unit of gamma detector elements, wherein the unit of gamma detector elements comprise a sub-set of the plurality of gamma detector elements within the module.

9. The imaging device of claim 1, wherein the gamma detector elements further comprise an integrated circuit.

10. The imaging device of claim 1, wherein the plurality of electronic communication components comprises a plurality of field programmable gate arrays, a plurality of array aggregators, a system control board, and a system on a chip (SoC).

11. The imaging device of claim 10, wherein each of the field programmable gate arrays communicate with one of the plurality of array aggregators.

12. The imaging device of claim 11, wherein each of the array aggregators comprises a field programmable gate array and communicates with the system control board and wherein the system control board communicates with the system on a chip (SoC).

13. The imaging device of claim 1, further comprising an Ethernet communication connection for communication with a remote system.

14. The imaging device of claim 1, wherein the cooling system is at least one system selected from the group consisting of: liquid cooling, forced air cooling, and passive air cooling.

15. An imaging device, comprising:
   a plurality of electronic communication components facilitating hierarchical communication from a plurality of gamma detector elements to a processor;
   the plurality of electronic communication components comprising a plurality of integrated circuits, a plurality of field programmable gate arrays, a plurality of array aggregators, a system control board, and the processor;
   wherein each gamma detector element comprises one of the plurality of integrated circuits and wherein the gamma detector elements are grouped into arrays, wherein an array of gamma detector elements comprises a subset of the gamma detector elements of the imaging device;
   wherein each of the integrated circuits of the arrays communicate with one of the plurality of field programmable gate arrays assigned to the corresponding array and wherein the arrays of gamma detector elements are grouped into units and wherein the units are grouped into drawers with a predetermined spacing wherein each of the drawers is mounted on a slideable mechanism, wherein each of the drawers is parallel to a bottom plane of the imaging device, wherein each of the plurality of modular components are field serviceable while maintaining the predetermined spacing between each of the gamma detector elements through travel of a corresponding drawer between a locked-closed position and a cantilevered position and wherein the predetermined spacing facilitates high resolution images across the plurality of modular components;

wherein the field programmable gate arrays for a corresponding drawer communicate with one of the plurality of array aggregators assigned to the corresponding drawer;

wherein the plurality of array aggregators communicate with the system control board and wherein the system control board communicates with the processor, the processor facilitating communication with a remote system.

16. The imaging device of claim 15, wherein the plurality of array aggregators comprises a plurality of field programmable gate arrays.

17. The imaging device of claim 15, wherein the system control board comprises a field programmable gate array.

18. The imaging device of claim 15, further comprising an Ethernet communication connection.

19. The imaging device of claim 18, wherein communication packets sent to the remote system are packaged into data packets for communication through the Ethernet communication connection, wherein the data packets are packaged based upon constraints of the Ethernet communication connection.

20. The imaging device of claim 19, wherein packaging the data packets comprises collecting and packaging a plurality of data communications into a single data packet.

21. A gamma imaging device, comprising:
a radiation-shielding enclosure comprising a casing and a lining comprising a lead alloy or tungsten alloy arranged within the casing to provide a complete radiation shield, wherein the enclosure comprises a top side, a bottom side, and four lateral sides, wherein one of the four lateral sides comprises a removable portion comprising a portion of the casing and a portion of the lining;
a plurality of modular components;
each of the plurality of modular components comprising a plurality of gamma detector elements comprising semiconductor crystals and integrated circuits and being removable from the imaging device, wherein the plurality of gamma detector elements comprises a subset of the gamma detector elements of the gamma imaging device;
the plurality of modular components being arranged such that the plurality of gamma detector elements are configured in an array configuration with each of the plurality of gamma detector elements having a predetermined spacing from each other gamma detector element, wherein each of the plurality of modular components are field serviceable while maintaining the predetermined spacing between each of the gamma detector elements;
a plurality of hierarchical electronic communication components facilitating communication from the plurality of gamma detector elements to a processor;
the plurality of electronic communication components comprising a plurality of integrated circuits, a plurality of field programmable gate arrays, a plurality of array aggregators, a system control board, and the processor;
wherein each gamma detector element comprises one of the plurality of integrated circuits and wherein the gamma detector elements are grouped into arrays comprising a plurality of gamma detector elements;
wherein each of the integrated circuits of the arrays communicate with one of the plurality of field programmable gate arrays assigned to the corresponding array and wherein the arrays of gamma detector elements are grouped into units comprising a plurality of arrays and wherein the units are grouped into drawers comprising a plurality of units, wherein the gamma imaging device comprises a plurality of drawers and wherein each of the plurality of drawers are mounted on a slideable mechanism, wherein each of the drawers is parallel to a bottom plane of the imaging device, wherein each of the plurality of arrays are field serviceable while maintaining the predetermined spacing between each of the gamma detector elements through travel of a corresponding drawer between a locked-closed position and a cantilevered position and wherein the predetermined spacing facilitates high resolution images across the plurality of arrays;
wherein the field programmable gate arrays for a corresponding drawer communicate with one of the plurality of array aggregators assigned to the corresponding drawer;
wherein the plurality of array aggregators comprise a plurality of field programmable gate arrays and communicates with the system control board and wherein the system control board comprises a field programmable gate array and communicates with the processor, the processor facilitating communication with a remote system; and
a cooling system.

* * * * *